United States Patent [19]

Arndt et al.

[11] Patent Number: 4,658,034

[45] Date of Patent: Apr. 14, 1987

[54] PROCESS FOR THE PREPARATION OF 2,6-DICHLOROBENZOXAZOLE

[75] Inventors: Otto Arndt, Hofheim am Taunus; Theodor Papenfuhs, Frankfurt am Main, both of Fed. Rep. of Germany

[73] Assignee: Hoechst Aktiengesellschaft, Fed. Rep. of Germany

[21] Appl. No.: 703,708

[22] Filed: Feb. 21, 1985

[30] Foreign Application Priority Data

Feb. 25, 1984 [DE] Fed. Rep. of Germany ....... 3406909

[51] Int. Cl.$^4$ ............................................ C07D 263/54
[52] U.S. Cl. ..................................... 548/217; 260/694
[58] Field of Search ......................... 548/217; 260/694

[56] References Cited

U.S. PATENT DOCUMENTS 2,099,781 11/1937 Waldron ............................. 260/694
3,284,294 11/1966 Sasse et al. ......................... 548/217
3,397,208 8/1968 Berman et al. ..................... 546/170
4,433,153 2/1984 Knorr et al. ........................ 548/217
4,517,370 5/1985 Becherer et al. ................... 548/217

FOREIGN PATENT DOCUMENTS 663153 7/1938 Fed. Rep. of Germany .
1164413 9/1964 Fed. Rep. of Germany .

OTHER PUBLICATIONS

Knorr et al, Chem. Abst., 96-142845k.
Handte et al, Chem. Abst., 98-107280s.
Syst. No. 4195, p. 47.
Becherer et al, Chem. Abst., 99-175748w.
Chem. Ber., 92, 1928 (1959).
Elderfield, Heterocyclic Compounds, vol. 5, p. 447.
Seidel, P. J., Pr. Chem., 42, 445–457 (1980).
McCoy, H., Am. Chem. J., 21, 111–167 (1899).
Sam, J. et al, J. Org. Chem., 23, 1500–1503 (1958).

*Primary Examiner*—Donald G. Daus
*Assistant Examiner*—Cecilia Shen
*Attorney, Agent, or Firm*—Connolly and Hutz

[57] ABSTRACT

A process for the preparation of 2,6-dichlorobenzoxazole, which comprises reacting 6-chlorobenzoxazolone in the presence of chlorine, phosphorus trichloride and phosphoryl chloride, or in mixtures of phosphorus pentachloride and phosphoryl chloride, at temperatures of 150° to 170° C., under pressure, the weight ratio of chlorine and phosphorus trichloride to phosphoryl chloride or of phosphorus pentachloride to phosphoryl chloride being 0.15:1 to 0.60:1.

4 Claims, No Drawings

PROCESS FOR THE PREPARATION OF 2,6-DICHLOROBENZOXAZOLE

The present invention relates to a new advantageous process for the preparation of 2,6-dichlorobenzoxazole. The preparation of 2-chlorobenzoxazole from 2-mercaptobenzoxazole (benzoxazolethiol) and chlorine or agents which eliminate chlorine (for example phosphorus pentachloride) is known (cf. J. pr. Chemie 42, 454 (1890), Am. Chem. J. 21, 117 (1899), J. Org. Chem. 23, 1500 (1958), Beilstein 27, Syst. No. 4195, DE-AS No. 1,210,617, NE-OS No. 6,505,511, GE No. 663,153, GE No. 1,164,413, EP No. 0,043,573, DE No. 3,207,153 and DE-OS No. 1,670,453).

However, the literature also contains information on the reaction of benzoxazolones (Z. Chemie 5 (1965), No. 5, pages 178-179) with the chlorinating agent pyrocatechylphosphorus trichloride (Z. Chemie 22 (1982), No. 4, pages 126-134), 2-chlorobenzoxazole being obtained from N-methylbenzoxazolone, for example, in a yield of 75% of theory. Methyl chloride is eliminated in this reaction. Benzoxazolone itself is clearly unsuitable as a starting compound because the yield of 2-chlorobenzoxazole is greatly reduced by the formation of N-benzoxazolylbenzoxazolone.

According to Chem. Ber. 92, 1928 (1959), 2-chlorooxazoles are obtained from oxazol-2-ones and phosphoryl chloride with the addition of triethylamine. Our own attempts to prepare 2,6-dichlorobenzoxazole from 6-chlorobenzoxazolone in this way were not successful.

The literature reference Heterocyclic Compounds, Volume 5, R. C. Elderfield, published by John Wiley (New York) and Chapman and Hall (London), page 447, excludes the possibility of preparing 2-chlorobenzoxazole from benzoxazolone and phosphorus pentachloride because chlorination on the nucleus cannot be avoided.

Although, according to EP No. 0,043,573 and DE-OS No. 3,207,153, 2,6-dichlorobenzoxazole can be prepared from 6-chloro-2-mercaptobenzoxazole, with or without solvent, in high purity (melting point 49°-50° C.) and in high yield (91% of theory), the preparation of the starting material 6-chloro-2-mercaptobenzoxazole from 5-chloro-2-aminophenol and alkali metal xanthate (DE-OS No. 3,008,225 and DP NO. 66,248) is expensive. Firstly, the removal of the sulfur dichloride thereby obtained, or its use elsewhere, presents a problem which is difficult to solve. Added to this is the fact that the production route to be taken from the patent literature proceeds via the following three problematical steps:

1. Partial chlorine exchange in the 2,4-dichloronitrobenzene to give 5-chloro-2-nitrophenol (DE-OS No. 2,939,056, Example 1) in the presence of onium-based phase transfer catalysts. The problem lies in the removal of the decomposition products of the catalysts, which are thermally unstable at the high reaction temperatures, and in the fact that a recycling technique must be introduced for the 2,4-dichloronitrobenzene.

2. Catalytic reduction of the 5-chloro-2-nitrophenol to 5-chloro-2-aminophenol. This presents problems due to dehydrohalogenation.

3. Ring closure to give mercaptobenzoxazole (EP No. 0,066,248). The removal of the hydrogen sulfide is expensive; furthermore, ethanol is formed.

By contrast, it has now been found, surprisingly, that 2,6-dichlorobenzoxazole can advantageously be prepared by reacting 6-chlorobenzoxazolone in the presence of chlorine, phosphorus trichloride and phosphoryl chloride or in mixtures of phosphorus pentachloride and phosphoryl chloride, at temperatures of 150° to 17020 C., preferably 155°-165° C., under pressure, the weight ratio of chlorine and phosphorus trichloride to phosphoryl chloride or of phosphorus pentachloride to phosphoryl chloride being 0.15:1 to 0.60:1.

The phosphoryl chloride used serves as a solvent in this reaction. It is used in the abovementioned ratio (to the chlorinating agents) in order to ensure that the chlorinating agent used (phosphorus pentachloride or a mixture of chlorine and phosphorus trichloride) and the hydrogen chloride formed in the reaction are diluted sufficiently.

The reaction time is 5-10 hours, a reaction time of 8 hours being most favorable as a rule. It has proved expedient to add ground sodium chloride and small quantities of dimethylformamide to the reaction mixture.

Since phosphorus pentachloride is formed from phosphorus trichloride and chlorine, as is known, it is understandable that it is also possible to use a mixture of chlorine and phosphorus trichloride in a molar ratio of 1:1 as the chlorinating agent instead of phosphorus pentachloride.

The technical effort involved in carrying out the process according to the invention is relatively small. However, it is necessary to have an autoclave whose inner wall is resistant towards the reaction mixture. A suitable autoclave is one which consists, for example, of a chromium-nickel alloy ("Hastelloy").

Contrary to the assertion put forward in the literature reference mentioned earlier (Heterocyclic Compounds, Volume 5, l.c.) that chlorination in the benzene nucleus makes it impossible to convert benzoxazolones to 2-chlorobenzoxazoles with phosphorus pentachloride, an investigation by gas chromatography/mass spectrometry of the reaction mixtures from the process discovered by us showed that only approx. 3% of trichlorobenzoxazoles and 4-5% of condensation products of mass 320 are formed together with a few components having up to 4 chlorine atoms, albeit in quantities of only approx. 1% in each case, and together with components of higher masses (up to approx. 700) and having up to 6 chlorine atoms.

When using benzoxazolone unsubstituted on the benzene ring, 2-chlorobenzoxazole is accompanied by up to equal quantities of 2,6-dichlorobenzoxazole. From this, it can be deduced that the chlorinating action of the mixture of phosphorus pentachloride and phosphoryl chloride on the nucleus is first directed mainly to the 6-position. If this position is already occupied, as in the case of 6-chlorobenzoxazolone, the chlorinating action of the mixture of phosphorus pentachloride and phosphoryl chloride on the nucleus is no longer a disadvantage. In that case, a definite product monochlorinated in the nucleus (2,6-dichlorobenzoxazole) is preferentially obtained. At least as far as the preparation of 2,6-dichlorobenzoxazole is concerned, the argument given in the cited literature reference Heterocyclic Compounds, Volume 5, is no longer meaningful and only serves to create a prejudice against this reaction possibility.

The 6-chlorobenzoxazolone used as the starting material can easily be prepared by the chlorination of benzoxazolone in dilute hydrochloric acid with hypochlorite or in concentrated hydrochloric acid with hydrogen peroxide (i.e. in the absence of organic solvent). (The yield of the 6-chlorobenzoxazolone from this reaction is 82% of theory, based on benzoxazolone, and the purity is 90%.)

Details or preferred embodiments of the process according to the invention are described below:

Because the handling of phosphorus pentachloride in the factory is unacceptable for reasons of toxicology and safety regulations, the phosphorus pentachloride can also be prepared by passing chlorine gas into phosphoryl chloride with which phosphorus trichloride has been mixed in a quantity equivalent to that of the chlorine. 1 mol of hydrogen chloride is liberated in the process according to the invention. For this reason and because of the vapor pressure of the phosphoryl chloride, pressures of 6–12 bar are established at the preferred reaction temperature of 155°–165° C.

Making the chlorination conditions milder by the addition of pyridine or by the addition of water (i.e. use of pyrophosphoryl chloride) detracts considerably from the result and is therefore to be avoided.

When the reaction mixture is worked up, distillative regeneration of the phosphoryl chloride is carried out first. The distillation residue is taken up in toluene water mixtures and a sediment is filtered off, the quantity of sediment being the smaller the higher the ratio of phosphorus pentachloride to phosphoryl chloride used. It contains more highly chlorinated phosphoric acid compounds. After separation of the phase of the filtrate, the toluene phase is washed with aqueous bicarbonate solution and then dried over calcium chloride, and the calcium chloride is filtered off. To regenerate the toluene, the filtrate is distilled to a residue. The distillation residue contains approx 75 percent by weight of 2,6-dichlorobenzoxazole, corresponding to a crude yield of 60% of theory (gas chromatography). The remainder is up to approx. 10 percent by weight of toluene and approx. 5% of 6-chlorobenzoxazolone/2,6-dichlorobenzoxazole condensation product of mass 320. The latter by-product increases and the degree of chlorination of the benzene ring decreases as the ratio of phosphorus pentachloride to phosphoryl chloride decreases.

The distillation residue is fractionated in vacuo to give 2,6-dichlorobenzoxazole with a purity of at least 97% (melting point 40°–44° C.) in a yield of over 90% of theory based on crude product, corresponding to 55% of theory based on 6-chlorobenzoxazolone.

2,6-Dichlorobenzoxazole is a valuable intermediate for the preparation of active substances for plant protection (DE-OS Nos. 2,640,730, 2,758,002 and 2,830,066; EP No. 0,062,905).

EXAMPLE 1

600 parts of phosphoryl chloride are placed in an autoclave made of a nickel-chromium alloy. 35 parts of ground sodium chloride, 35 parts of recrystallized 6-chlorobenzoxazolone (melting point 190°–194° C.), 1 part of dimethylformamide and 100 parts of phosohorus pentachloride are then introduced. The autoclave is closed, heated to 155° C. and then stirred for 8 hours at 155° C. A pressure of approx. 8 bar is established. The pressure in the autoclave is then let down at 25° C. and 640 parts of phosphoryl chloride are subsequently distilled off up to 120° C. and 133 mbar.

The distillation residue is stirred with 200 parts of toluene and 200 parts of ice-water and the sediment (15 parts) is filtered off from the mixture. After separation from the aqueous phase, the toluene filtrate is washed with 100 parts of 5% sodium bicarbonate solution. After the aqueous phase has been separated off, the toluene solution is dried over calcium chloride. The toluene is distilled off at normal pressure. The following are found in the distillation residue (28 parts) by combined gas chromatographic/mass spectroscopic measurement: 21 parts of 2,6-dichlorobenzoxazole (purity 75%), 2 parts of toluene, 0.8 part of trichlorobenzoxazole (mass 221), 0.1 part of tetrachlorobenzoxazole (mass 255), 1.1 parts of condensation product $C_{14}H_6O_3N_2Cl_2$ (mass 320) and 0.3 part of condensation product $C_{14}H_5O_3N_2Cl_3$ (mass 354). The remainder consists of involatile constituents or constituents of low volatility. The content of saponifiable chlorine is 16.5% (theory 18.9%) and the total chlorine content is 35.5% (theory 37.7%).

The crude product solidifies at 25° C. to a crystalline mass. Fractionation at 3 mbar over a distillation bridge heated to 70° C. gives 19.4 parts of 97% pure 2,6-dichlorobenzoxazole, corresponding to 18.6 parts calculated as 100% pure=50% of theory, based on 6-chlorobenzoxazolone (melting point 40°–44° C.)

EXAMPLE 2

The procedure described in Example 1 is followed, but 150 parts of phosphorus pentachloride are used and the reaction time is only 5 hours. 620 parts of phosphoryl chloride are obtained on distillative regeneration. Working-up of the 90 parts of distillation residue gives
 (a) 12 parts of filtration residue (from taking-up in toluene/water);
 (b) 26 parts of crude 2,6-dichlorobenzoxazole (after distillation of the toluene) containing 21 parts of 2,6-dichlorobenzoxazole.

The content of saponifiable chlorine is 19.5%. The crude product solidifies at 25° C. to a crystalline mass.

EXAMPLE 3

35 parts of 6-chlorobenzoxazolone are reacted with 250 parts of phosphorus pentachloride and 450 parts of phosphoryl chloride for 8 hours at 165° C. The final pressure is 12 bar. The reaction mixture is added slowly to 2000 parts of ice and 870 parts of toluene, which are stirred vigorously. No sediment is formed in this process. The toluene phase is separated off, washed with bicarbonate solution and water and then dried over calcium chloride and filtered. After distillation of the toluene, 34 parts of distillation residue are obtained. It contains 23 parts of 2,6-dichlorobenzoxazole (corresponding to a purity of 67%), approx. 3 parts of trichlorobenzoxazole (mass 221), approx. 0.5 part of tetrachlorobenzoxazole (mass 255), approx. 0.3 part of pentachlorobenzoxazole (mass 289) and approx. 0.3 part of condensation product $C_{14}H_6O_3N_2Cl_2$ of mass 320. The rest contains the involatile constituents and constituents of low volatility (including components of mass 700 and having 6 chlorine atoms).

The content of saponifiable chlorine is 17.0% (theory 18.9%) and the total chlorine content is 41.7% (theory 37.7%).

The crude product solidifies at 25° C. to a crystalline mass. After fractionation, 20.7 parts of 2,6-dichlorobenzoxazole calculated as 100% pure=55% of theory, based on 6-chlorobenzoxazolone, are obtained.

EXAMPLE 4

The procedure described in Example 1 is followed, but no phosphorus pentachloride is used. The pressure is 6 bar at 160° C. and the filtration residue from stirring with toluene/water amounts to 11 parts. After distillation of the toluene, the distillation residue weighs only 8-9 g and is a pulverulent solid. 75% of condensation product of masses 320 and 354 is found in the solid by combined gas chromatographic/mass spectrometric analysis. The rest is 6-chlorobenzoxazolone (=starting material). No 2,6-dichlorobenzoxazole could be detected. The content of saponifiable chlorine is only 2.1%, the total chlorine content being 20.2%.

EXAMPLE 5

The procedure described in Example 1 is followed, but 35 parts of a 6-chlorobenzoxazolone of only 88% purity and melting point 178°-181° C. are used, corresponding to 0.18 mol (crude product from the chlorination of benzoxazolone). Working-up is carried out as described in Example 3. No insoluble sediment is obtained. 31 parts of crude product are obtained (after distillation of the toluene) together with 22 parts of 2,6-dichlorobenzoxazole (corresponding to a purity of 70%) and 8 parts of components elutable at a late stage. The content of saponifiable chlorine is 19.9%.

The yield is 22 parts calculated as 100% pure=0.116 mol=64% of theory based on 6-chlorobenzoxazolone, or 52% of theory based on benzoxazolone.

What is claimed is:

1. A process for the preparation of 2,6-dichlorobenzoxazole, which comprises reacting 6-chlorobenzoxazolone in the presence of chlorine, phosphorus trichloride and phosphoryl chloride, or in mixtures of phosphorus pentachloride and phosphoryl chloride, at temperatures of 150° to 170° C., under pressure, the weight ratio of chlorine and phosphorus trichloride to phosphoryl chloride or of phosphorus pentachloride to phosphoryl chloride being 0.15:1 to 0.60:1.

2. A process as claimed in claim 1, wherein the preparation is carried out in a said mixture of phosphorus pentachloride and phosphoryl chloride.

3. A process for the preparation of 2,6-dichlorobenzoxazole, which comprises reacting 6-chlorobenzoxazolone under pressure at a temperature in the range of 150° to 170° C. in the presence of a mixture comprising:
   (a) phosphoryl chloride, and either
   (b1) phosphorus pentachloride, or
   (b2) chlorine and phosphorus trichloride, the weight ratio of (b1) or (b2) to (a) being in the range of 0.15:1 to 0.06:1.

4. A process as claimed in claim 3, wherein said mixture comprises phosphoryl chloride and phosphorus pentachloride.

* * * * *